United States Patent [19]

Doury-Berthod et al.

[11] Patent Number: 5,062,961
[45] Date of Patent: Nov. 5, 1991

[54] PROCESS FOR THE DETERMINATION OF THE CONCENTRATION OF AN IONIC OR IONIZABLE SOLUTE IN ION EXCHANGE CHROMATOGRAPHY

[75] Inventors: Michele Doury-Berthod, Gif sur Yvette; Pierre Giampaoli, Montrouge, both of France

[73] Assignee: Commissariat a l'Energie Atomique, Paris, France

[21] Appl. No.: 499,470

[22] PCT Filed: Oct. 26, 1989

[86] PCT No.: PCT/FR89/00558

§ 371 Date: Aug. 3, 1990

§ 102(e) Date: Aug. 3, 1990

[87] PCT Pub. No.: WO90/04780

PCT Pub. Date: May 3, 1990

[30] Foreign Application Priority Data

Oct. 27, 1988 [FR] France ............................... 88 14038

[51] Int. Cl.⁵ ........................................... B01D 15/08
[52] U.S. Cl. ................................. 210/656; 210/198.2; 436/161; 73/61.1 C
[58] Field of Search ............... 210/656, 198.2; 422/70; 436/161; 73/61.1 C

[56] References Cited

FOREIGN PATENT DOCUMENTS 0274396 7/1988 European Pat. Off. ............ 210/656

OTHER PUBLICATIONS

Doury-Berthod, "Theoretical Approach of Dual-Column Ion Chromatography", Analytical Chemistry, vol. 57, No. 12, Oct. 1985, pp. 2257-2263.
Gjerde, "Sodium and Potassium Benzoate and Benzoic Acid as Eluents for Ion Chromatography", Analytical Chemistry, vol. 53, No. 14, Dec. 1981, pp. 2324-2327.
Os, "Linear Calibration in Ion Chromatography By Calculating Total Amounts of Sample From Measured Conductivity Data", Analytica Chimica Acta, 156 (1984), pp. 169-180.
Okada, "Sensitivity of Non-Suppressed Ion Chromatography Using Divalent Organic Acid As Eluents", Journal of Chromatography, 284 (1984), pp. 149-156.
Analytical Chimica Acta, vol. 156, 1984, Elsevier Science Publishers B.V. (Amsterdam, NL), J. J. van Os et al., "Linear calibration in ion chromatography by calculating total amounts of sample from measured conductivity data", pp. 170-173.

*Primary Examiner*—Ernest G. Therkorn
*Attorney, Agent, or Firm*—Oblon, Spivak, McClelland, Maier & Neustadt

[57] ABSTRACT

Process for the determination of the concentration of a solute in a solution whose constituents are known.

The first step is to determine the concentration of the hydrogen ions with the aid of an implicit equation as a function of the dissociation constant of the constituents of the solution and the unknown concentration of the solute and then the concentration of the constituents of the solution to which a measurement is sensitive. The concentration of the solute is obtained by comparing the theoretical signal function with the experimental signal.

Particular application to ion exchange chromatography systems with or without chemical suppression.

10 Claims, 1 Drawing Sheet

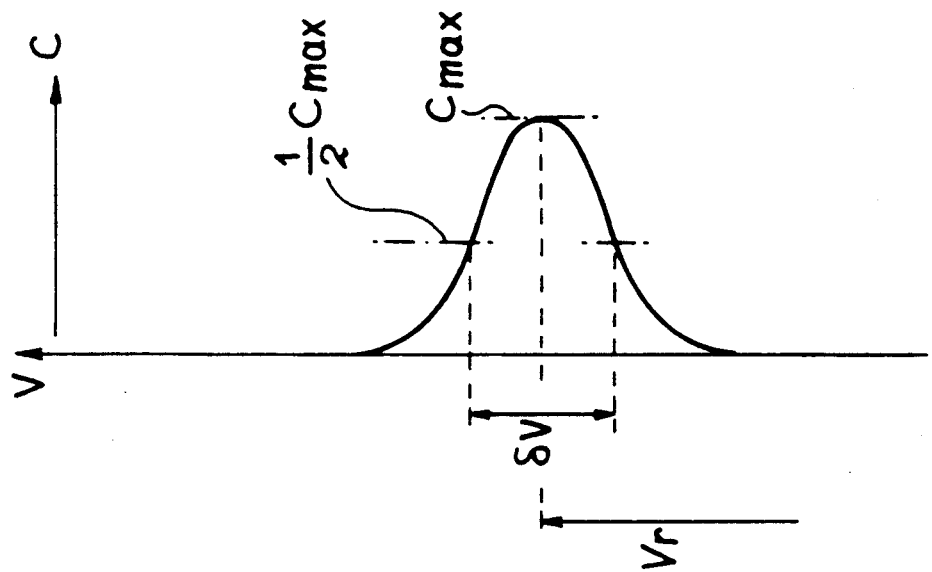
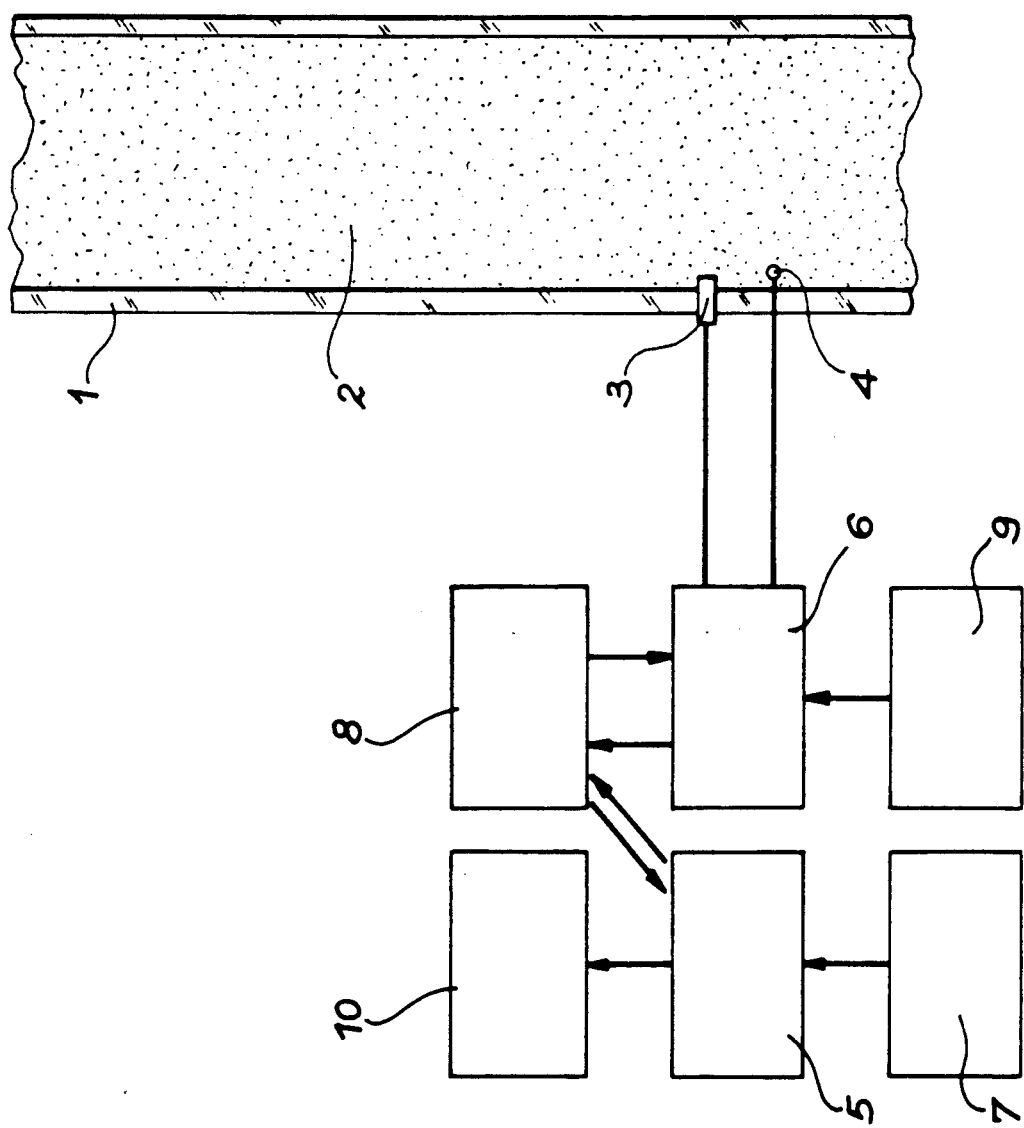

PROCESS FOR THE DETERMINATION OF THE CONCENTRATION OF AN IONIC OR IONIZABLE SOLUTE IN ION EXCHANGE CHROMATOGRAPHY

DESCRIPTION

The invention relates to a process for determining the concentration of an ionic or ionizable solute in ion chromatography, or more specifically ion exchange chromatography, by calculating the concentration of hydrogen ions.

Ion chromatography consists of introducing a sample of the solution containing the solute to be quantified at the top of a column packed with an ion exchanger and to circulate continuously therein another solution having a known composition and called the eluent.

The solute and the species of the eluent are at least partly dissolved. The ion exchanger is a divided porous solid, which is insoluble in water, but which on contact therewith is impregnated with it and which contains functional groups grafted in a fixed quantity. These are ionized, the charge of the grafted ionic species being compensated by that of ions having an opposite sign and called exchange ions. The latter are mobile and can undergo exchange with other ions (exchangeable ions) of the same sign present in the solution external of the water-impregnated ion exchanger particles, which constitute the stationary phase. When it is in prolonged contact with the eluent, the stationary phase assumes a constant composition, the exchange ions being solely constituted by exchangeable ions of the eluent. The eluent (or eluent solution) is the constant composition solution continuously supplied by means of a pump to the top of the column. The mobile phase is the solution flowing in the column in contact with the stationary phase.

Following their injection, the exchangeable ions of the solute gradually advance in the column, under the effect of the continuous percolation of the eluent, via ion exchange reactions with the ions of the eluent contained in the mobile and stationary phases. A measuring cell located at a clearly defined point in the column and in particular at its outlet, detects a characteristic quantity or magnitude of the composition of the mobile phase at this point, this phase being called the eluate. This composition is dependent on the equilibria involved in the column upstream of the cell.

In the case of the injection of a mixture of solutes, the different exchangeable ions of said solutes migrate at different speeds, which are a function of the relative affinities of said species for the stationary phase.

The conductivity of the eluate is frequently the measured characteristic magnitude and said method is used both in systems with and without chemical suppression. Thus, it is standard practice to subdivide these procedures into two groups, as a function of whether a so-called chemical suppression reactor is or is not interposed between the separating column and the detector. The object of this reactor, which is especially designed for conductance or conductometric detection, is to reduce the residual conductance of the eluent whilst increasing that of the solute to be analyzed, by a bias of the ion exchange reactions and acidbase neutralization. As a result of their very principle, chemical suppression systems lead to signal-to-noise ratio values which are higher than in systems without chemical suppression.

In order to determine the concentration of a solute in the eluate without passing via the plotting of a calibration curve, it is essential to have the mathematical expression of the analysis signal. The latter is a function of the concentrations of the ionic species constituting the eluate, as well as the concentrations of the ionic species constituting the eluent. The comparison of the experimental signal with its theoretical expression makes it possible to deduce the total concentration of the solute, in all its forms, present in the eluate. This operation can be reproduced for all solutes successively reaching the detector, recognition being brought about by means of a specific locating method predetermined for the chromatographic system used, such as the speed of advance in the separating column. In the particular case of conductometry or conductance, there is only an interest in the concentration of the ionic species of the eluate, because only these contribute to the signal.

Various authors have already proposed such mathematical expressions in particular cases and reference can be made to the articles which have appeared in Analytical Chemistry, 1981, 53, pp. 2324–2327 and 1984, 56, pp. 1177–1182, in Journal of Chromatography, 1984, 284, pp.149–156 and Analytical Chemistry Acta, 1984, 156, pp.169–180.

In general terms, these expressions only apply for special simplified cases, which imply restrictive hypotheses regarding the nature of the eluent or the solute and which sometimes contain errors. It is in particular necessary to take account of possible displacements of the dissociation equilibria of the eluent species causing variations in the proportions of its different acid-base forms in the mobile phase. A correct general mathematical expression of the signal has been supplied in a particular case by the inventors and is described in Analytical Chemistry, 1985, 57, pp.2257–2263.

This mathematical expression has only been developed for chemical suppression chromatography and leads to a complicated formulation of the theoretical signal (relation 15 of said article). In the remainder of said article interest is only attached to the case where the solute is in the form of a single anionic species in the measuring cell. Moreover, it was necessary to assume that the solute was present in the separating column containing the stationary phase in the form of a single anionic species (possibly differing from the preceding type), that the eluent species were only present in the measuring cell in the non-dissociated form and in their molecular acid form in equilibrium with the corresponding monoanionic conjugate base and finally that the hydroxide ion concentration was negligible compared with that of the other ions.

BRIEF DESCRIPTION OF THE DRAWING

The sole figure shows a plot of concentration versus eluate volume and an apparatus for performing the process of the invention.

DESCRIPTION OF THE PREFERRED EMBODIMENTS

The clear existence of these inadequacies led to the process according to the invention, which is valid for both chromatography types, for eluents constituted by weak or strong monoprotic or polyprotic acid solutions, a salt of a monoprotic acid or a mixture of the acid and its salt, a salt of a diprotic acid or a mixture of several acid-base forms of said acid and for any ionizable solute whose anion belongs to the acid-base system of a weak or strong monoprotic or polyprotic acid. The anion can be present in the separating column and in the chemical suppression reactor in a number of different forms. The process obtained leads to an exact determination, without approximation, of the theoretical signal curve.

These advantages are obtained as a result of a formulation of the concentration of the hydrogen ions solely as a function of the concentration of the species constituting the solute and without directly involving the dissociation coefficient of the molecular acid-base form of the acid-base eluent system.

More specifically, the invention relates to a process for the determination of the concentration of a solute in an eluate, the solute being at least partly dissociated in the form of at least one anionic species, the eluate being also constituted by hydrogen ions and species belonging to the acid-base system of an eluent at least partly dissociated in the form of at least one anionic species, the dissociation of these species and of those of the solute producing hydrogen ions, the composition of the eluate being more particularly governed by exchange reactions of ions previously used in the separating column between the anionic species of the eluent and those of the solute, as well as possibly other chemical reactions and in particular ion exchange and acid-base neutralization reactions in a so-called chemical suppression reactor, characterized in that it comprises calculating the concentration of the hydrogen ions solely as a function of the concentration of the solute with the aid of dissociation constants of acid species liable to be involved, invariable proportions for a given solute in a given chromatographic system of anions of the solute, which are exchanged in the separating column with eluent species of different valencies, proportions of the species of the solute dissolved in the separating column, the total concentration of the constituent species of the eluent and the concentration of the cationic species associated with the saline eluent species in the eluent, then calculating the concentrations in the eluate of at least some of its constituents, as a function of the solute concentration with the aid of the concentration of the hydrogen ions, then calculating a theoretical signal function consisting of superimposing effects resulting from concentration variations of the constituents of the eluate whose concentration has been calculated in the preceding stage and finally placing an experimental signal on the theoretical signal function in order to deduce therefrom the concentration of the solute.

The concentration of the hydrogen ions is advantageously calculated by successive iterations. The experimental signal and the theoretical signal curve can be respectively obtained by measuring and calculating the conductivity of the eluate.

The process can be entirely automated. It is possible to recognize the nature of a solute on the basis of the eluate volume which has flowed since the introduction of said solute up to the maximum of its elution peak, after which a succession of measurements is carried out which, by comparison with the theoretical signal curve, supply the successive concentrations of the solute in the detector and finally the total solute quantities obtained by integration on the chromatographic peak.

The chromatographic system may or may not have chemical suppression.

A specific example will now be described in an illustrative and non-limitative manner using a weak diacid eluent with a possible saline form in an ion chromatography system. The solute is here a weak polyacid. On the basis of this example, it is easily possible to arrive at the equations and relations governing other eluents and solutes.

The composition of the eluate is governed by the following equilibria:

acid-base dissociation of the acid species of the eluent

$$H_2L \rightleftharpoons H^+ + HL^- \quad (1)$$

$$\text{and } HL^- \rightleftharpoons H^+ + L^{2-} \quad (2)$$

acid-base dissociation of the acid form of the solute, which can be described by an average equilibrium

$$H_nX \rightleftharpoons mH^+ + H_{n-m}X^{m-} \quad (3),$$

dissociation of the water

$$H_2O \rightleftharpoons H^+ + OH^- \quad (4)$$

ion exchange equilibria between the anionic species of the solute and those of the eluent, between the stationary phase and the mobile phase in a separating column

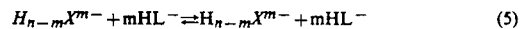

$$H_{n-m}X^{m-} + m\overline{HL^-} \rightleftharpoons \overline{H_{n-m}X^{m-}} + mHL^- \quad (5)$$

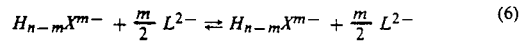

$$H_{n-m}X^{m-} + \frac{m}{2}\overline{L^{2-}} \rightleftharpoons \overline{H_{n-m}X^{m-}} + \frac{m}{2}L^{2-} \quad (6)$$

where the symbols surmounted by a bar relate to the species present in the stationary phase. The equilibria (1), (2), (3) and (4) are characterized by the constants $k_i$, $K_{a1}$, $K_{a2}$, which are known to the user and given by the following relations:

$$k_i = [H^+].[OH^-] \quad (7)$$

$$K_{a1} = [H^+].[HL^-].[H_2L]^{-1} \quad (8)$$

$$K_{a2} = [H^+].[L^{2-}].[HL^-]^{-1} \quad (9)$$

A unique solute dissociation reaction was assumed, but in reality the solute can be present in the form of a mixture of anionic species, m then designating the average charge of the anionic species of the solute in the eluate and may consequently not be an integer, but this does not change the following reasoning.

The nature of the mean or average species $H_{n-m}X^{m-}$ of the solute is determined on the basis of dissociation constants $K_i$ of the different acid species of said solute and which are obviously known to the user and expressed by:

$$K_i = [H^+][H_{n-i}X^{i-}][H_{n-i+1}X^{(i-1)-}]^{-1} \quad (10)$$

The value of m is determined on the basis of the relation:

$$m = \sum_{i=1}^{i=n} a_{n-i} \cdot i \quad (11)$$

in which $a_{n-i}$ represents the proportion of the species $H_{n-i}X^{i-}$ in the eluent and expressed by:

$$a_{n-i} = \frac{[H_{n-i}X^{i-}]}{\sum_{i=0}^{i=n}[H_{n-i}X^{i-}]} \quad (12)$$

$C_E$, $C_M$ and $C_X$ respectively referred to the total concentration of the constituent species of the eluent, the concentration of the cationic species associated with the saline eluent species in the eluent and the total concentration of the constituent species of the solute in the eluate.

The coefficient $\beta$ designates the solute fraction exchanging with the divalent species of the eluent in the separating column, i.e. $\beta$ is equal to 0 if the stationary phase only contains HL− ions and $\beta = 1$ if it only contains $L^{2-}$ ions.

The mass balance of the species of the eluent in the eluate is expressed by the relation:

$$[H_2L] + [HL^-] + [L^{2-}] = C_E - m\left(1 - \frac{\beta}{2}\right)C_X \quad (13)$$

The electroneutrality law of this system is expressed by the relation:

$$[H^+] = [OH^-] + [HL^-] + 2[L^{2-}] + m[H_{n-m}X^{m-}] - [M^+] \quad (14)$$

On referring to relations (7) to (13), relation (14) is equivalent to relation (15):

$$[H^+] = \frac{K_i}{[H^+]} + \frac{K_{a1}\left[\left(C_E - m\left(1 - \frac{\beta}{2}\right)C_X\right)\right]}{[H^+]F_H} + \frac{2K_{a1}\cdot K_{a2}\left[C_E - m\left(1 - \frac{\beta}{2}\right)C_X\right]}{[H^+]^2 F_H} + mC_X - C_M \quad (15)$$

In relation (15), the only unknown is $C_x$, because the concentration $C_E$ and $C_M$ of the eluent are chosen by the user. $\beta$ was determined in a preceding stage, as will be discussed hereinafter. Coefficient $F_H$ was introduced for facility reasons and its expression is defined in the equation:

$$F_H = 1 + \frac{K_{a1}}{[H^+]} + \frac{K_{a1}\cdot K_{a2}}{[H^+]^2} \quad (16)$$

Contrary to the earlier article published by the Inventors, the relation (15) giving the concentration of the hydrogen ions on the basis of the electroneutrality law is an implicit equation, which takes account of the acid - base dissociation equilibria of all the acid species present in the eluate, whereas relation (11) of the earlier article only considered the dissociation equilibrium of the molecular acid form of the acid - base system of the eluent, which was expressed through the dissociation coefficient $\alpha$.

For an adequate number of plausible values of $C_X$, an iterative procedure is used for calculating the corresponding hydrogen ion concentration. It is then possible for each of the values of $C_X$ to calculate the concentrations of the anions: OH-, HL- and $L^{2-}$ with the aid of relations (17), (18), (19) and (20) which can be deduced from the preceding relations:

$$[H_2L] = \frac{C_E - \left(1 - \frac{\beta}{2}\right)mC_X}{F_H} \quad (17)$$

$$[HL^-] = \frac{K_{a1}\left[C_E - \left(1 - \frac{\beta}{2}\right)mC_X\right]}{[H^+]F_H} \quad (18)$$

$$[L^{2-}] = \frac{K_{a1}K_{a2}\left[C_E - \left(1 - \frac{\beta}{2}\right)mC_X\right]}{[H^+]^2 F_H} \quad (19)$$

$$[OH^-] = \frac{k_i}{[H^+]} \quad (20)$$

In the frequently used case of a detection by conductometry, the theoretical signal is given by the expression:

$$\Delta G = \frac{1000}{k}\left[\sum_{i=1}^{n}\lambda^o\left[\frac{1}{2}(H_{n-i}X^{i-})\right]i a_{n-1}C_X + \lambda^o_{HL} - \Delta[HL^-] + 2\lambda^o_{\frac{1}{2}L}2 - \Delta[L^{2-}] + \lambda^o_H + \Delta[H^+] + \lambda^o_{OH} - \Delta[OH^-]\right] \quad (21)$$

In this expression, G designates the conductance of the eluate in microsiemens, $\lambda o$ the equivalent limit conjunctivities in siemens.cm$^{-2}$.mole$^{-1}$ of the ions in question at the temperature of the experiment, k the constant of the detector cell expressed in cm$^{-1}$, $a_{n-i}$ the proportions of each of the ionic species of the solute, which can be calculated with the aid of the dissociation constants of the solute and $\Delta$ the difference of the magnitude which it precedes with respect to the state without solute ($C_x = 0$). The concentration of the cation of the saline species of the eluent is invariable and is consequently not involved in the expression of the signal. The equivalent limit conductivity of a species at the temperature t can be calculated by means of the relation:

$$(\lambda o)_t = (\lambda o)_{25}[1 + 0.01825(t-25)] \quad (22)$$

The theoretical signal $\Delta G$ can be determined as a function of the concentration $C_x$. In an automatic analysis system, it is stored in the memory in the form of a library function. During the elution of a chromatographic peak a series of conductivity measurements is carried out in order to obtain experimental signals which are compared with the library function. Thus, an experimental value of concentration $C_x$ is deduced therefrom by measurement. The total solute quantity injected into the chromatographic column is finally given by an integration as a function of the eluate volume flowing during the measurements, i.e. in accordance with the relation:

$$q_E = \int C_x dv \quad (23)$$

A description will now be given of the calibration procedure of the system more particularly involving the determination of $\beta$.

A known solute quantity $q^o$ is injected. The experimental signal of the chromatographic peak is plotted. For using values of said quantity $q^o$ and the volume corresponding to the mid-height peak with $\delta V$, it is possible to calculate the maximum theoretical concentration $C_{XM}$ of the solute in the peak by assuming a Gaussian distribution and using the relation:

$$C_{XM} = \frac{q^o}{\delta V} \sqrt{\frac{5.54}{2\pi}} \quad (24)$$

The concentration calculated in this way for the maximum height of the peak is introduced into the relation (15) and the value of $\beta$ is adjusted until the theoretical signal supplied by the relation (21) corresponds to the measured signal, so that an estimate of $\beta$ is available.

As this estimate is only approximate, verification calculations are then carried out. The theoretical signal curve $\Delta G(C_X)$ corresponding to the estimated value of $\beta$ is calculated and then, by comparison with experimental signals, a calculation takes place of the solute concentrations at a certain number of points of the peak and relation (23) is integrated in order to verify if the real injected solute quantity is found. In the negative, the value of $\beta$ is adjusted until the estimate of the injected quantity coincides with the real quantity.

The thus performed calibration is definitive for a given chromatographic system and for a given solute and it is pointless to repeat it before each analysis. It is also pointless when the eluent species are only present in the stationary phase in the form of a single ionic species.

The analysis of an unknown solute firstly takes place by monitoring the appearance of chromatographic peaks. For each of them the peak start and finish volumes are plotted, together with the retention volume of the peak, i.e. the volume at the top of the peak, as well as the width of the peak at mid-height for a concentration equal to half the maximum solute concentration $C_{MAX}$ of the volume corresponding to the eluate volumes which have flowed since the injection of the sample. It is therefore possible to identify the nature of the solute and detect a poor operation of the chromatographic system (partial or total overlap of the chromatographic peaks, variations of these peaks, etc.). The coefficients characterizing it $\lambda^o$, $a_{n-i}$, m and $\beta$) are read on memories and for each discretization point of the peak, the concentration $C_X$ of the solute is determined by the application and identification of a point on the theoretical signal curve at the experimental signal. The identified solute quantity is finally calculated with the aid of relation (23).

The first tests carried out in particular on chloride and nitrate ions with different eluent buffers, particularly sodium phthalate and benzoate, demonstrated that the process was accurate.

A system for performing the process is diagrammatically shown in the drawing. It comprises a chromatographic column 1 filled with a resin 2 between the interstices of which the mobile phase flows. A conductance cell 3 and a thermometer 4 are in contact with the eluate. The system comprises an arithmetic unit 5, a peak analysis unit 6, a data bank 7, a file 8, an input keyboard 9 and a printer 10.

The arithmetic unit 5 comprises logic means for in particular carrying out the calculations corresponding to relations (19), (21) and (23).

The peak analysis unit 6 is connected to the cell 3 and to the thermometer 4. It detects variations of the signals emitted by the cell 3, i.e. the appearance and shape of the chromatographic peaks and also measures temperature. It is provided with time measuring means enabling it to regularly record the signals of the cell 3 and measure the flowed eluate volumes. It is therefore able to identify the unknown solutes on the basis of their retention volume.

The data bank 7 contains known data regarding the most widely used solutes and eluents and in particular their acid-base dissociation constants and the equivalent limit conductivities of their ionic species at 25° C.

The file 8 contains data directly usable for the identification of the solutes and the calculation of the concentrations and theoretical signals, i.e. in particular $a_{n-i}$, m, $\beta$ and the equivalent limit conductivities corresponding to the real temperature of the eluent measured by the thermometer 4. These equivalent limit conductivities are calculated by the arithmetic unit 5 with the aid of the relation 22.

The input keyboard 9 makes it possible to put into action the peak analysis unit 6 so that it will analyze a given peak and introduce into the file 8 and possibly the data bank 7 the data concerning the new solutes or eluents. The printer 10 essentially indicates the nature of the identified solutes and their concentration in the sample.

The process is clearly not limited to chromatographic systems without chemical suppression and to conductance methods. It can also be used for radiation absorption, pH and electrochemical characteristic measurement methods. The useful physicochemical quantities for the calculations can then be different from those indicated hereinbefore, but are accessible after solving equation (15).

For chemical suppression chromatographic systems, it is also necessary to have the proportions $a'_{n-1}$ of each of the species resulting from the dissociation of the solute after chemical suppression, as well as the average charge m' of the solute ions in said solution. The solutions used in the calculations are the same, with the exception of relation (14), in which $[M^+]=0$ and in which m is replaced by m', (15) in which $C_m=0$ and $mC_x=m'C_x$, and relation (21) in which $a_{n-i}=a'_{n-i}$. m' and $a'_{n-i}$ are calculated by the expressions (11) and (12) in which m=m' and $a_{n-i}=a'_{n-i}$.

It is finally clear that the invention is applicable to processes in which interest is only attached to the concentration of certain solutes in a complex mixture.

We claim:

1. Process for the determination of the concentration of a solute in an eluate, the solute being at least partly dissociated in the form of at least one anionic species, the eluate being also constituted by hydrogen ions and species belonging to the acid-base system of an eluent at least partly dissociated in the form of at least one anionic species, the dissociation of these species and of those of the solute producing hydrogen ions, the composition of the eluate being more particularly governed by exchange reactions of ions previously used in the separating column between the anionic species of the eluent and those of the solute, said process comprising: calculating the concentration of the hydrogen ions solely as a function of the concentration of the solute with the aid of dissociation constants of acid species liable to be involved, invariable proportions for a given solute in a given chromatographic system of anions of the solute, which are exchanged in the separating column with eluent species of different valencies, proportions of the species of the solute dissolved in the separating column, the total concentration of the constituent species of the eluent and the concentration of the cationic species associated with the saline eluent species in the eluent, then calculating the concentrations in the eluate of at least some of its constituents, as a function of the solute concentration with the aid of the concentration of the hydrogen ions, then calculating a theoretical signal function consisting of superimposing effects resulting from concentration variations of the constituents of the eluate whose concentration has been calculated in the preceding stage and finally placing an experimental signal on the theoretical signal function in order to deduce therefrom the concentration of the solute and indicating the concentration of the solute.

2. Process for determining the concentration of a solute according to claim 1, characterized in that the eluate contains hydroxide ions and in that the relation of the ionic product of the water is used for determining the concentration of the hydrogen ions.

3. Process for the determination of the concentration of a solute according to any one of the claims 1 or 2, characterized in that the concentration of the hydrogen ions is calculated by an iterative calculation.

4. Process for the determination of the concentration of a solute according to claim 1, characterized in that the solute is an acid.

5. Process for the determination of the concentration of a solute according to claim 1, characterized in that the eluent is produced by the dissociation of its species, hydrogen ions and other cations, the concentration of said other cations being used for calculating the concentration of the hydrogen ions.

6. Process for determining the concentration of a solute according to claim 1, characterized in that the experimental signal and the theoretical signal curve are respectively obtained by measuring and calculating the conductivity of the ionic constituents of the eluate.

7. Process for determining the concentration of a solute according to claim 1, characterized in that several successive concentration measurements of the solute are carried out on a chromatographic peak to obtain, by integration, the total solute quantity present in the eluate.

8. Process for determining the concentration of a solute according to claim 1, characterized in that the proportions of the different anionic species of the eluent present in the eluate are determined by a preliminary calibration, by injecting a known solute quantity into the column and by recording the corresponding experimental signal variations.

9. Process for determining the concentration of a solute according to claim 8, characterized in that the preliminary calibration consists of plotting the eluate volume which has flowed between two readings, on either side of a maximum experimental signal corresponding to the apex of a chromatographic peak, for which the experimental signal is the mean value of the maximum experimental signal and a signal corresponding to the absence of solute, calculating a maximum theoretical concentration of the solute, plotting the maximum experimental signal and then calculating a maximum experimental concentration of the solute as a function of the proportions of various anionic species of the eluent present in the eluate, deducing an approximation of said proportions by placing the maximum theoretical concentration on the maximum experimental concentration function, deducing the experimental concentration of the solute at these points with the aid of the approximation of said proportions and readings of experimental signals of points distributed over the chromatographic peak, integrating the experimental concentrations of the solute at these points as a function of the eluate volumes which have flowed between them to obtain an approximate experimental solute quantity, comparing the approximate experimental solute quantity and the known injected solute quantity and adjusting the approximation of said proportions, followed by the repetition of the stages of deducing the experimental concentrations of the solute, integration and comparison until the approximate experimental solute quantity and the known injected solute quantity coincide.

10. Process for determining the concentration of a solute according to claim 1, wherein the composition of the eluate is further governed by ion exchange and acid-based neutralization reactions which occur in a chemical suppression reactor.

* * * * *